United States Patent [19]

Loveless

[11] Patent Number: 4,469,910

[45] Date of Patent: Sep. 4, 1984

[54] METHOD FOR THE OLIGOMERIZATION OF ALPHA-OLEFINS

[75] Inventor: Frederick C. Loveless, Cheshire, Conn.

[73] Assignee: Uniroyal, Inc., New York, N.Y.

[21] Appl. No.: 530,333

[22] Filed: Sep. 8, 1983

[51] Int. Cl.³ ............................................... C07C 3/21
[52] U.S. Cl. ................................... 585/511; 502/152; 526/185; 585/510; 585/522; 585/532
[58] Field of Search ............... 585/510, 511, 512, 517, 585/518, 519, 521, 522, 525, 529, 532, 312, 324, 329; 526/185; 502/152

[56] References Cited

U.S. PATENT DOCUMENTS

| | | | |
|---|---|---|---|
| 3,278,262 | 10/1966 | Poe et al. | 585/511 |
| 3,629,150 | 12/1971 | Addy | 585/511 |
| 3,637,896 | 1/1972 | Jones et al. | 585/512 |
| 4,041,098 | 8/1977 | Loveless | 585/521 |
| 4,197,420 | 4/1980 | Ferraris et al. | 585/329 |
| 4,380,684 | 4/1983 | Fowler et al. | 585/522 |

FOREIGN PATENT DOCUMENTS

| | | | |
|---|---|---|---|
| 246110 | 5/1960 | Australia | 585/522 |
| 59304 | 10/1973 | Japan | 585/511 |

Primary Examiner—Delbert E. Gantz
Assistant Examiner—A. Pal
Attorney, Agent, or Firm—Andrew D. Maslow

[57] ABSTRACT

A process is provided for oligomerizing alpha-olefins comprising contacting in a reaction zone under reaction conditions: (a) alpha-olefins having at least three carbon atoms; (b) an aluminum compound having the formula $R_3Al$, wherein R is an hydrocarbyl group and (c) a cocatalyst which is hydrocarbyl halide having at least one halogen group reactive with said aluminum compound, elemental bromine or elemental iodine.

5 Claims, No Drawings

METHOD FOR THE OLIGOMERIZATION OF ALPHA-OLEFINS

This invention relates to novel catalyst systems useful for polymerizing alpha-olefins and to the process in which this catalyst system is used to obtain hydrocarbon oligomers useful as lubricants, hydraulic fluids, heat transfer fluids and the like.

It is known to prepare polymeric lubricating oils by contacting an alpha-olefin with a metal halide catalyst, such as $AlCl_3$ and limiting the extent of polymerization to between about 10 and 20 percent conversion of monomer to polymer as disclosed in U.S. Pat. No. 2,559,984. In the process disclosed in this patent, the reaction temperature can vary between about $-20°$ and $40°$ C. However, if conversion of the alpha-olefin is greater than about 20%, the resultant product has a poor viscosity index and pour point.

This prior art utilizes solid catalysts and teaches the preparation of low viscosity oligomers by virtue of limiting conversion of monomer to 20%. Unless such commercially unattractive low conversions are maintained, products having poor viscosity index and high pour point are obtained. The instant invention utilizes soluble catalysts and produces, in high conversion, oligomers having high viscosity index and excellent low temperture viscosity.

It is also known to obtain synthetic lubricating oils by contacting one or more alpha-olefins of $C_6$-$C_{14}$ range at a temperature of about $0°$ to $50°$ C. with a catalyst system formed from three types of components: (a) alkyl aluminum sesquichloride, dialkyl aluminum monochloride or monoalkyl aluminum dichloride; (b) titanium tetrachloride; and (c) an oxygen-containing organic compound which is either an oxirane or a methyl allyl ether. Such a process is disclosed in U.S. Pat. No. 3,206,523.

U.S. Pat. No. 3,179,711 discloses a similar but modified method wherein the third component in the catalyst system is tetra-alkyl silicate, in which the alkyl groups each have 1–4 carbon atoms and are unbranched, rather than an oxygen-containing hydrocarbon compound.

The catalysts described in the above patents are anionic-coordination (Ziegler) catalysts which can be used to oligomerize alpha-olefins, but which are characterized by their extremely slow polymerization rate (for example, twenty hours are frequently required for high monomer conversion) and frequent necessity for using solvents.

The instant invention provides a process where the reaction rates of the catalyst are very rapid and the use of solvent is not necessary. These features lend themselves to the rapid production of oligomer in a batch or continuous process. The highly desirable continuous process is impractical when the above coordination catalysts of the prior art are used.

The preparation of synthetic lubricating oils by polymerizing an alpha-olifin with $AlCl_3$ at $57°$ C. has also been revealed to produce, e.g., a polyoctene having a viscosity index of 104 and a pour point of $-20°$ F. (Industrial and Engineering Chemistry, Vol. 23, No. 6, June, 1931, pp. 604–611.)

A method for producing lubricating oils by treating a petroleum distillate containing a high percentage of unsaturated hydrocarbons in the presence of $AlCl_3$ at a temperature of between $300°$ and $400°$ F. has also been disclosed in U.S. Pat. No. 1,309,432.

The use of solid $AlCl_3$ described in the two above references if, of necessity, limiting in the versatility of the process utilizing them for the production of oligomers. The properties of the oligomers obtained, such as pour point and viscosity index, from such an acidic catalyst are defensive because of the extensive rearrangements of the carbon structure of the oligomers, especially in the latter reference above where very high temperatures are utilized.

The aluminum chlorides of the prior art have very low solubility in the more widely used alpha-olefins. They also can cause polymerization upon contact with these monomers. For this reason, solutions of aluminum chloride in monomer cannot be utilized in the type of continuous process made possible by the instant invention. According to the instant invention, aluminum alkyls may be dissolved in the alpha-olefin monomer and the solution, then fed to a reaction zone in a continuous process. The monomer to aluminum ratio can be held constant throughout the polymerization in the process according to the instant invention.

In the instant invention the disadvantages of the prior art are partially overcome, since the lower acidity and solubility of the catalyst of the instant invention lead to a greater versatility in choice of process and to oligomers having superior properties because of their less rearranged, more regular structure.

U.S. Pat. Nos. 3,637,503 (Gianetti) and 2,525,788 (Fontana et al.) describe the preparation of alpha-olefin oligomers utilizing aluminum halides "activated" by hydrohalide acids. These catalysts are also insoluble in the monomer and the described methods are batch polymerizations involving hydrocarbon solvents and long reaction times, none of which are necessary limitations of the present method.

The prior art patents describe variations of the above aluminum halide processes, wherein numerous compounds are utilized to modify the highly acidic catalyst prior to its utilization. Typical of such patents are U.S. Pat. No. 4,066,715 and German Offen. 2,617,403.

U.S. Pat. No. 4,041,098 describes a method for oligomerizing alpha-olefins utilizing a catalyst prepared by combining alkyl aluminum chlorides with a variety of alkyl halides in the presence of alpha-olefin. The main teaching of this patent lies in the preparation of relatively low molecular weight oligomers ($C_{20}$ to $C_{60}$) in reasonable conversion. It points out that polymerizations having a high proportion of oligomer greater than $C_{60}$ result in products which have pour points too high to be useful. The preferred polymerization temperature disclosed in the reference is $100°$–$140°$ C. The alkyl halides disclosed are chlorides, bromides or iodides wherein not more than one halogen is attached to any single carbon in the molecule. In this process, low boiling oligomers are removed by distillation and the resulting product is optionally hydrogenated to improve its oxidative stability.

The instant invention differs from the above reference in in that while U.S. Pat. No. 4,041,098 limits the alkyl aluminum halides utilized to alkyl aluminum chlorides, the present invention teaches the use of trialkyl aluminum compounds.

In their practical application as catalysts, the trialkyl aluminum compounds have advantages over the alkyl aluminum chlorides of U.S. Pat. No. 4,041,098, in that they are less corrosive and less likely to cause undesirable acidic reactions, such as polymerization of monomers in which they are dissolved.

Thus, the prior art teaches the oligomerization by catalysts containing aluminum halides or alkyl aluminum halides of alphaolefins of $C_3$ to $C_{14}$ and higher, such as propylene, butene, pentene, hexene, heptene, octene, nonene, decene, undecene, dodecene, tridecene and tetradecene to produce a wide range of molecular weight oligomers useful as lubricants, hydraulic fluids and the like. Most techniques utilize insoluble cataysts and solvents and are not amenable to continuous polymerization. Cationic catalysts based on alkyl aluminum chlorides are described as being useful for the preparation of moderately viscous oligomers in the temperature range of 100°–200° C. The molecular weight obtained in such systems is usually controlled by variations in catalyst concentration and temperature.

It would be advantageous, therefore, to oligomerize a high percentage of alpha-olefins utilizing a method and catalyst wherein continuous polymerization can be performed easily, where molecular weight can be controlled by temperature and catalyst concentration. The instant invention teaches polymerization methods wherein all these advantages can be attained. This combination of advantages is not taught or suggested in any of the prior art methods.

Both high and low viscosity alpha-olefin oligomers are known to be useful in the production of functional fluids such as lubricants. Low viscosity oligomers (e.g., having kinematic viscosity from 4 to 30 cSt. at 100° C.) are frequently used as the main base stock for synthetic lubricants, frequently with the addition of a thickener which can be a high molecular weight rubbery "V.I. improver" or a viscous oil. More viscous polyalpha-olefins (e.g., 40–1000 cSt. at 100° C.) are generally added to low viscosity, natural or synthetic fluids to increase their viscosity to a given S.A.E. Grade, while also frequently improving their viscosity index. An ideal oligomerization method, therefore, is one which, by proper choice of polymerization conditions and catalyst, can produce a wide range of viscosities with minimum changes in the process variables. The present invention teaches how catalyst changes alone can be made which permit production of a very wide viscosity range of products useful either as a base stock or as a thickener.

According to the present invention, synthetic hydrocarbon fluids are prepared by contacting one or more alpha-olefin monomers with a soluble catalyst system prepared by reacting in the presence of monomer a trialkyl aluminum with bromine, iodine, an organo-chloride, an organo-bromide or organo-iodide. The three necessary ingredients may be brought together into the reactor means in any convenient manner with the restriction that monomer must be present when the aluminum compound and cocatalyst are contacted. Any operator skilled in the art can easily assess that there are several variations possible by which the ingredients may be combined. Thus, for instance, monomer, aluminum compound and cocatalyst can all be directed separately into the reaction means or one or both of the catalyst ingredients can can be dissolved in all or part of the monomer prior to contacting in the reactor means. The operation of this invention requires that the overall haolgen to aluminum ratio should be at least 2.5 to 1. Normally the level of aluminum compound utilized is such that the molar ratio of monomer to aluminum is from 20 to 200. The halide cocatalyst usage is regulated, as dictated by the aluminum level, to achieve an overall active halogen to aluminum ratio of at least 2.5 to 1 or higher. A convenient procedure for performing the invention is to dissolve the organo-aluminum compound in an alpha-olefin and combine it with a solution of organo halide compound also in the alpha-olefin. The combining can take place, for example, in a stirred autoclave or a pipe reactor. Reaction to form the product is very rapid and continuous polymerization can be achieved by removing reaction mixture at the same rate the feed ingredients are being introduced.

Frequently, depending on the choice of catalyst, slightly longer "residence times" in the reactor are necessary to produce higher viscosity oligomers. This is easily accomplished by increasing reactor size for a given feed rate or reducing feed rate for a given reactor size. Additionally, since it has been found that viscosity is sensitive to reaction temperature, means for cooling the reaction mass are beneficial in the production of high viscosity fluids.

Conversely, with a given catalyst combination, low residence times and higher temperatures can be utilized to produce low viscosity fluids.

After the reaction is complete, monomer consumption is normally greater than 95% and usually greater than 99%. The crude reaction product is then optionally "shortstopped" with water or a low molecular weight alcohol, followed by a catalyst removal step, such as an aqueous wash. Other methods of catalyst removal, such as filtration, absorption or centrifugation can also be utilized. The catalyst-free product is subjected to an evaporative distillation to remove low boiling oligomers (e.g., below $C_{25}$) and hence, insure low volatility in the final product. The oil is optionally hydrogenated before or after distillation by conventional methods employing a metallic-catalyst and hydrogen for production of fluids having outstanding oxidation-stability in harsh environments. Normally, an iodine number below 5 and preferably below 2 will produce an oligomer with excellent oxidation stability as illustrated in U.S. Pat. No. 4,110,234.

The alkyl aluminum compounds operable in this invention are of the formula $R_3Al$ where:

R is a hydrocarbyl group, e.g., methyl, ethyl, propyl, ipropyl, butyl, i-butyl, hexyl, octyl, decyl, dodecyl, phenyl, tolyl and the like.

The halogen cocatalysts operable in the invention are $Br_2$ and $I_2$.

The organo halides operable in the invention are organo chlorides, organo bromides or iodides having one or more halogen atoms per molecule wherein at least one halogen per organohalide is not bound to an aromatic ring. The organo halides can be primary, secondary or tertiary aliphatic compounds, allylic halides or benzylic halides. Typical of such halides are t-butyl chloride; t-butyl bromide; t-butyl iodide; allyl bromide; allyl iodide 1,2-dibromobutane; 2,3-dibromobutane; 3,4-dibromopentane; 1,4-dibromobutene-2; 1,4-diiodobutene-2; 1,2-dibromocyclohexane; methallyl bromide; methallyl iodide; benzyl bromide; benzyl iodide; 1,2,7,8-tetrabromo-octane; 1-bromo-2-phenylethane; 1,2-dibromo-1-phenylethane; 1,2,5,6-tetrabromocyclooctane and the like. Also useable as organo halide cocatalysts are higher molecular weight saturated or unsaturated molecules which have been halogenated to contain an average of one or more bromine or iodine atom per molecule, for instance, brominated mineral oil, brominated high molecular weight polyalpha-olefins, brominated wax or brominated rubbers or plastics providing the resultant products have the proper required solubility in alpha-olefins.

The monomers of use in this invention are any which are polymerizable by cationic (acid) catalysis. Thus, alpha-olefins of $C_3$ to $C_{14}$ carbon atoms can be used to prepare polyalpha-olefins. Alpha-olefins from $C_6$ to $C_{12}$ are preferred in homopolymers because of their ease of handling (liquid) and the excellent properties of their oligomers. Copolymers from mixtures of alpha-olefins can also be prepared and such methodology finds benefits particulary in blends of low molecular weight and high molecular weight monomers, whose copolymers have properties superior to mixtures of their homopolymers.

Aside from straight-chain alpha-olefins, terminal olefins with branching can be polymerized using the methods of the instant invention. For instance, useful oligomers can be made from "vinylidene" type monomers, such as 2-methylpropylene (isobutylene), 2-ethylhexene-1, 2-butyloctene-1 and the like. Monomers having terminal double bonds and branches remote from the unsaturation may also be easily polymerized. An example of such a monomer would be 4-methylhexene-1.

It should be obvious to anyone skilled in the art that a variety of useful functional fluids can be prepared utilizing various mixtures of the above monomers.

As with any polymerization involving organometallic catalysts, all ingredients and equipment used should be as free from air, moisture and other potential catalyst poisons as possible. Equipment can be dried by heat and vacuum while monomers can be distilled, passed through dessicant columns or stored over dessicants. Manipulation of the ingredients before and during polymerization should stress anaerobic conditions and inert gas atmospheres where necessary.

In practice, the level of organoaluminum compound utilized should be at least 0.1% by weight of the total monomer. The halogen or organohalide useage should be such to provide an ultimate total halogen to aluminum ratio of at least about 2.5/1.

While there is no upper limit on the amount of either catalyst component, little is gained by utilizing greater than 5% by weight of the organometallic compounds or by operating at halogen to aluminum ratios greater than 25/1.

The temperatures operative in the practice of this invention normally range from 0° C. to 200° C., although temperatures outside this range can be utilized. In non-adiabatic polymerizations, heat transfer capability may be necessary to maintain steady state conditions.

The invention is further illustrated by and will become more clear from a consideration of the following examples which should not be construed to limit the scope of the invention.

EXAMPLE I

This example illustrates the preparation of an oligomer of decene-1 utilizing a catalyst system based on a trialkyl aluminum compound.

A dry, nitrogen filled 4-necked, 500 ml. round bottomed flask was fitted with:
(1) A thermometer
(2) A 125 ml. dropping funnel having a pressure equalizing side arm and a stopper
(3) A similar dropping funnel connected to a nitrogen source and bubbler to induce a slight nitrogen pressure in the flask
(4) An overhead mechanical stirrer Beneath the flask was placed a bath of cold water on a jack permitting periodic cooling of the flask as required.

Into dropping funnel (2) was syringed 100 ml. of previously dried decene-1 and 10.5 ml. (96 millimoles) of tertiary butyl chloride. Into dropping funnel (3) was syringed 100 ml. of decene-1 and 10 ml. of a 1.6 molar solution of triethyl aluminum in hexane. The overall chlorine to aluminum ratio for the reaction was thus set at 6 to 1.

The contents of funnels (2) and (3) were added dropwise to the stirred flask at such a rate that addition was completed in 90 minutes (1.22 ml. per minute from each funnel). During the addition period, temperature was maintained at 42°±2° C. by raising or lowering of the water bath below the flask.

The reaction mixture was stirred for an additional 15 minutes. The catalyst was then destroyed by the addition of 10 ml. of methyl alcohol. The precipitated catalyst residues thus formed were removed by passing the thick slurry through a bed of F-20 alumina (Aluminum Company of America). Optionally, a solvent such as hexane may be added to the reaction product prior to filtration to avoid inordinately long filtration times.

The clear crude oligomeric product was then subjected to a vacuum distillation to remove any constituents boiling below 150° C. at 0.1 mm. The residual product, obtained in over 90% yield had a kinematic viscosity at 100° C. ($K.V._{100}$) of 20.4 cSt. and a $K.V._{40}$ of 166.28 cSt. The viscosity index of the fluid was 143.

EXAMPLE II

This example demonstrates that the allyl chloride cocatalyst of U.S. Pat. No. 4,041,098 is not operable wth triethyl aluminum following the procedures outlined in U.S. Pat. No. 4,041,098.

In an experiment performed identically to Example I, the tertiary butyl chloride in funnel (2) was replaced with 4.24 ml. of allyl chloride. When the contents of funnels (2) and (3) were added to the reaction flask, no oligomerization of the decene occurred. The experiment was repeated three times, wherein the reaction flask was heated with an oil bath to 100° C., then 120° C., and then 140° C. prior to the addition of reactants. In all cases, no reaction occurred. Doubling of triethylaluminum and allyl chloride levels also produced no results.

EXAMPLE III

This example demonstrates how the combination of triethyl aluminum and allyl chloride can be used as oligomerization catalysts.

Following the procedure of Example I, 20.8 ml. of a 1.25 molar solution of triethyl aluminum were added to the decene in dropping funnel (3) and 8.48 ml. of allyl chloride were added to the decene in dropping funnel (2). As shown in Example II, addition of these two ingredients to the reaction flask produces no oligomerization, whereas we have shown in Example I that treithyl aluminum and tertiary butyl chloride do produce oligomerization.

In this example, prior to the addition of the ingredients in funnels (2) and (3), 0.5 ml. of tertiary butyl chloride was added to the reaction flask, followed by the addition of 5 ml. from funnel (2). An instantaneous oligomerization of the decene in the flask occurred. Following this, the contents of funnels (2) and (3) were added to the flask exactly as described in Example I. A vigorous and complete oligomerization of the monomer ensued, producing an oil having K.V.$_{100}$=41.35 cSt., K.V.$_{40}$=437.98 cSt. and a V.I.=145.

Thus, when oligomerization is initiated with tertiary butyl chloride, it can be continued with allyl chloride to produce an oligomer having a viscosity greater than that obtained from tertiary butyl chloride cocatalyst in Example I.

EXAMPLE IV

This Example illustrates how elemental bromine can be utilized as a cocatalyst with triethyl aluminum wherein bromine is added directly to funnel (2) to produce 1,2-dibromodecane in situ.

Following the procedure of Example 1, 16 ml of a 1.6 molar solution of triethyl aluminum (0.0256 moles) was dissolved in decene in funnel (2) and 4.19 ml bromine was added to decene in funnel (2), to give an overall Br/Al ratio of 6.36. Oligomerization was initiated by adding 0.5 ml of 25% ethyl aluminum sesquibromide and 5 ml from funnel (2) to the reaction flask. This was necessary because of the reluctance of pure trialkyl aluminum to react with alkyl bromides at ordinary temperatures. Reaction was nearly instantaneous and thereafter funnels (2) and (3) were added as in Example I. The product oligomer had KV$_{100}$ of 107.07 cSt. and a V.I. of 178.

EXAMPLE V

In an experiment run using exactly the same ingredients as Example IV, the bromine, 1-decene and triethyl aluminum were all added independently by utilizing a third dropping funnel. The oligomerization reaction proceeded very similarly as in Example IV and produced a product of K.V.$_{100}$=97.4 cSt.

This shows that the ingredients of this invention may be combined in any convenient way with the catalyst and/or cocatalyst being optionally and independently premixed with all, none, or part of the monomer prior to combining in the reactor.

EXAMPLE VI

This example illustrates the use of tertiary butyl bromide as a cocatalyst with triethyl aluminum to prepare an oligomer of decene.

The polymerization was run exactly as in Example I, except that funnel (2) contained 12.3 ml (14.6 grams) of t-butyl bromide dissolved in 109.2 ml decene-1 and funnel (3) contained 20.8 ml of a 1.25 normaly triethy aluminum in hexane solution dissolved in 95.8 ml. decene-1. The product oligomer had a KV$_{100°\ C.}$ of 126 cST., a KV$_{40°\ C.}$ of 1539 cSt. and a V.I. of 182.

Thus tertiary aliphatic bromides are operative in this invention and produce oligomers of high viscosity.

EXAMPLE VII

Example IV was repeated exactly except that 0.0256 moles of triisobutyl aluminum was used in place of the triethyl aluminum. Surprisingly the product has a KV$_{100}$ of only 43.83 cSt. This finding indicates that viscosity control of oligomers is possible with trialkyl aluminum based catalysts by utilizing triethyl aluminum to produce high viscosity, as in Example VI, triisobutyl aluminum to produce lower viscosity and blends of the two to produce intermediate viscosity oligomers.

EXAMPLE VIII

This example illustrates the use of bromine adducts to internal olefins as cocatalysts with the aluminum alkyls of this invention. Typical of such adducts is 2,3-dibromobutane, readily prepared by the addition of bromine to butene-2.

Thus, in a polymerization run as in Example I, 3.3 ml (5.94 grams) of 2,3-dibromobutane were added to 108.5 ml of decene in funnel (2) and 10.4 ml of 1.25 N TEA were added to 96.5 ml of decene-1 in funnel (3). Reaction was initiated with EASB as in Example IV and the polymerization continued by adding the ingredients in funnels (2) and (3) as in Example I. The resultant product had a KV$_{100}$ of 82.5 cSt. and a V.I. of 165.

Thus adducts of bromine to internal olefins are demonstrated to be excellent cocatalysts with the aluminum alkyls of this invention.

EXAMPLE IX

This example illustrates the use of 1,4-dibromobutene-2 with triethyl aluminum as a catalyst for decene-1 oligomerization.

In a polymerization conducted as in Example I, solutions of 20.8 ml. of 1.25 N triethyl aluminum in 92.8 ml. decene-1 and 6.3 ml. 1,4-dibromobutene-2 in 112.2 ml. of decene-1 were combined over a 90 minute interval at a temperature of 42°±2° C. After workup as in Example I, the product oil had a K.V.$_{100}$ of 38 cSt. and a V.I. of 146.

EXAMPLE X

This example illustrates the use of elemental iodine as a cocatalyst with triethyl aluminum.

The oligomerization was performed essentially as described in Example I, except that 9.52 grams of iodine were added to the reaction flask prior to reaction and 10 ml. of a 1.25 N solution of triethyl aluminum dissolved in 200 ml. of decene-1 were added over a 90 minute period while maintaining a temperature of 42°±2° C.

The oligomerization proceeded smoothly, and all monomers had disappeared (as evidenced by the infra spectrum) shortly after addition was complete. After catalyst removal and stripping, the oligomeric product had a KV$_{100}$ of only 13.1 cSt. This is in sharp contrast to the high viscosity oligomers obtained in Examples IV and V wherein bromine is used as the cocatalyst.

What is claimed is:

1. A process for oligomerizing alpha-olefins comprising contacting in a reaction zone under reaction conditions: (a) alpha-olefins having at least three carbon atoms; (b) an aluminum compound having the formula R$_3$Al, wherein R is an hydrocarbyl group; and (c) a cocatalyst which is hydrocarbyl halide having at least one halogen group reactive with said aluminum compound, elemental bromine or elemental iodine.

2. The process of claim 1 wherein the overall molar ratio of reactive haolgen to aluminum is at least 2.5.

3. The process of claim 2 wherein the overall molar ratio of monomer to aluminum is at least 3.

4. The process of claim 3 wherein the overall molar ratio of monomer to aluminum is at least 10.

5. The process of claim 4 wherein the overall molar ratio of monomer to aluminum is from 20 to 200.

* * * * *